US00PP37696P2

(12) United States Plant Patent
Wyckstandt

(10) Patent No.: US PP37,696 P2
(45) Date of Patent: Sep. 15, 2026

(54) ***AGAPANTHUS* PLANT NAMED 'Su Casa'**

(50) Latin Name: ***Agapanthus* hybrid**
Varietal Denomination: Su Casa

(71) Applicant: Tim Wyckstandt, Aalter (BE)

(72) Inventor: Tim Wyckstandt, Aalter (BE)

(73) Assignee: VAN VLIET NEW PLANTS B.V., Stroe (NL)

( * ) Notice: Subject to any disclaimer, the term of this patent is extended or adjusted under 35 U.S.C. 154(b) by 0 days.

(21) Appl. No.: 19/422,434

(22) Filed: Dec. 17, 2025

(51) Int. Cl.
*A01H 6/04* (2018.01)
*A01H 5/02* (2018.01)

(52) U.S. Cl.
USPC ..... Plt./398

(58) Field of Classification Search
USPC ..... Plt./398
CPC ..... A01H 6/04; A01H 5/02
See application file for complete search history.

*Primary Examiner* — Keith O. Robinson
(74) *Attorney, Agent, or Firm* — Penny J. Aguirre

(57) ABSTRACT

A new cultivar of *Agapanthus* plant named 'Su Casa' that is characterized by its floriferous and long flowering period, its light violet-blue flowers, its blooms that are present on young plants, and its tall plant height.

3 Drawing Sheets

Botanical classification: *Agapanthus* hybrid.
Varietal denomination: 'Su Casa'.

CROSS REFERENCE TO RELATED APPLICATIONS

The application is related to a European plant breeders' rights application filed on Dec. 8, 2022, application No. 2022/2863. This application is co-pending with U.S. Plant Patent Applications filed for plant patents derived from the same breeding program that is entitled *Agapanthus* Plant Named 'A19002' (U.S. Plant patent application Ser. No. 19/422,442, *Agapanthus* Plant Named 'A21001' (U.S. Plant patent application Ser. No. 19/422,443), *Agapanthus* Plant Named 'A22004' (U.S. Plant patent application Ser. No. 19/422,445, and *Agapanthus* Plant Named 'Vitro002' (U.S. Plant patent application Ser. No. 19/442,451.

BACKGROUND OF THE INVENTION

The present invention relates to a new and distinct cultivar of *Agapanthus* of hybrid origin and will be referred to hereafter by its cultivar name, 'Su Casa'. 'Su Casa' represents a new perennial grown for landscape and container use.

The new cultivar was derived from a controlled breeding program by the Inventor in Aalter, Belgium. The goal of the breeding program was to develop a new cultivar of *Agapanthus* with a vigorous growth rate that flowers as a young plant. The new cultivar arose from open-pollination of *Agapanthus* 'Marijke' (not patented) in July of 2018. The male parent is therefore unknown. 'Su Casa' was selected as a single unique plant from the resulting seedlings of the cross in June of 2019.

Asexual propagation of the new cultivar was first accomplished by division by the Inventor in Aalter, Belgium in July of 2019. Asexual propagation by division and tissue culture utilizing meristematic tissue has determined that the characteristics of the new cultivar are stable and are reproduced true to type in successive generations.

SUMMARY OF THE INVENTION

The following traits have been repeatedly observed and represent the characteristics of the new cultivar. The characteristics in combination distinguish 'Su Casa' as a distinct cultivar of *Agapanthus*.

1. 'Su Casa' exhibits a floriferous and long flowering period.
2. 'Su Casa' exhibits light violet-blue flowers.
3. 'Su Casa' exhibits blooms as a young plant.
4. 'Su Casa' exhibits a tall plant height (typically 80 cm).

The female parent of 'Su Casa' differs from 'Su Casa' in having less flowers, less leaves, and blooms that are not present until plants are older. 'Su Casa' can be most closely compared to the *Agapanthus* cultivars 'African Queen' (not patented) and 'Aga04051' (not patented). Both 'African Queen' and 'Aga04051' are similar to 'Su Casa' in having violet-blue flowers. 'African Queen' differs from 'Su Casa' in having a less compact plant habit, a less floriferous blooming habit, and darker violet-blue flowers. 'Aga04051' differs from 'Su Casa' in having a less floriferous blooming habit and slightly darker violet-blue flowers.

'Su Casa' can also be compared to the co-pending cultivars of *Agapanthus*; 'A19002', 'A21001', 'A22004' and 'Vitro002'. 'A19002' differs from 'Su Casa' in having white flowers. 'A21001' differs from 'Su Casa' in having deep blue flowers with blue filaments. 'A22004' differs from 'Su Casa' in having violet-blue flowers with a darker central stripe on the tepals. 'Vitro002' differs from 'Su Casa' in having white flowers with yellow filaments.

BRIEF DESCRIPTION OF THE DRAWINGS

The accompanying color photographs illustrate the overall appearance and distinct characteristics of the new *Agapanthus*. The photographs were taken of plants 19 months in age of 'Su Casa' as grown in an unheated poly-covered tunnel in a 19-cm circular container in Aalter, Belgium.

Figure 1:
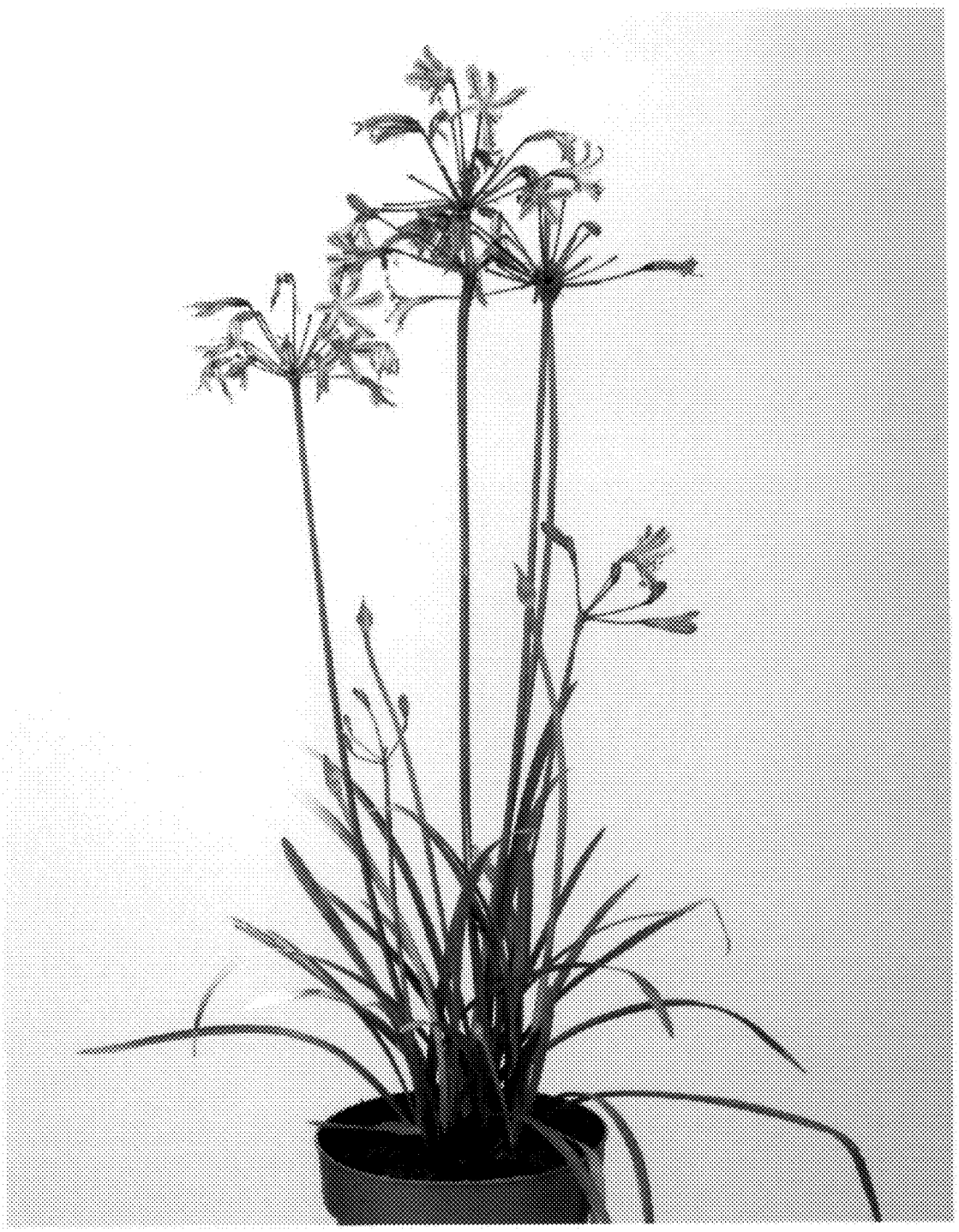

The photograph in FIG. 1 provides a side view of a plant of 'Su Casa' in bloom.

Figure 2:
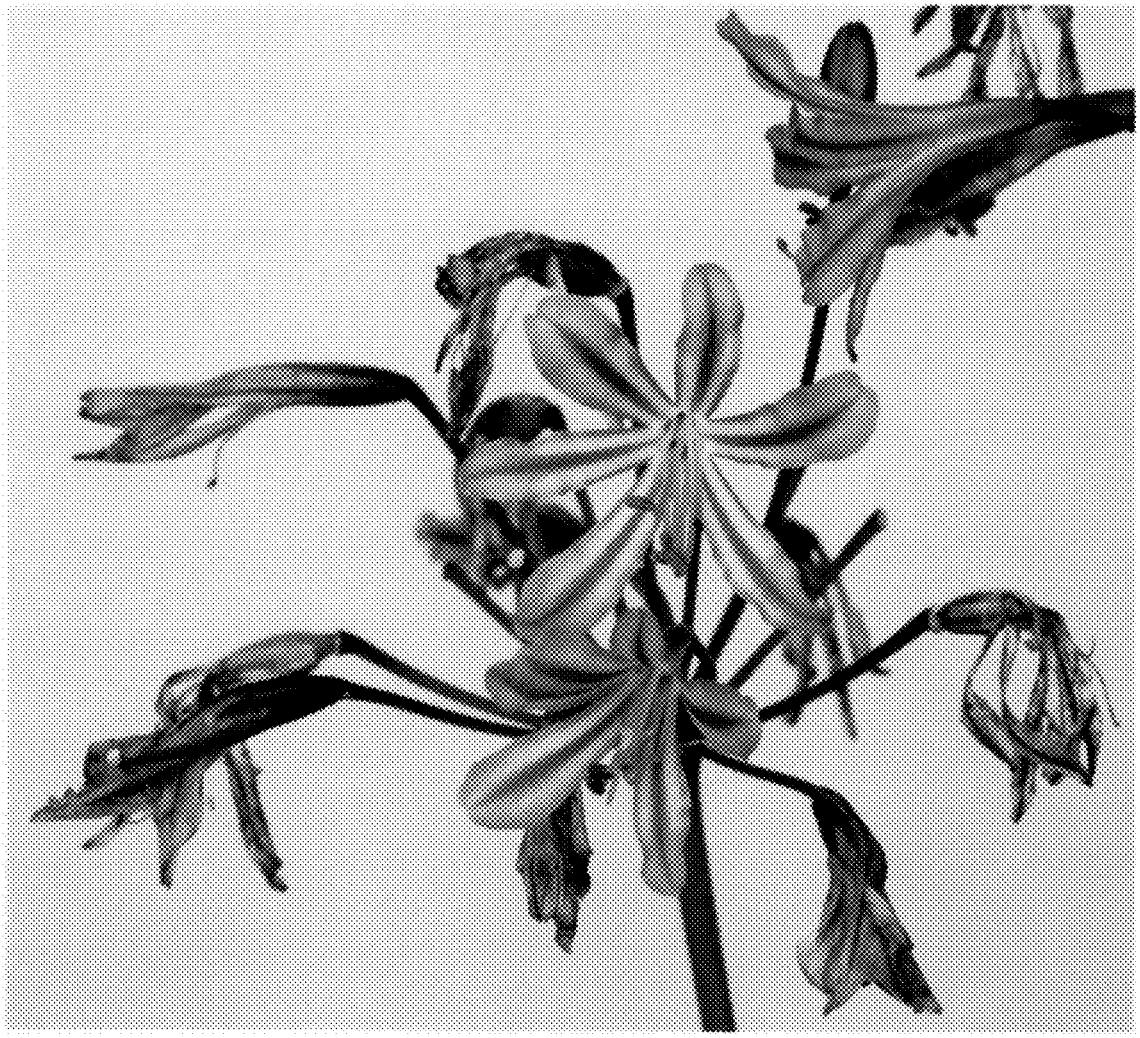

The photograph in FIG. 2 provides a close-up view of the flowers of 'Su Casa'.

Figure 3:
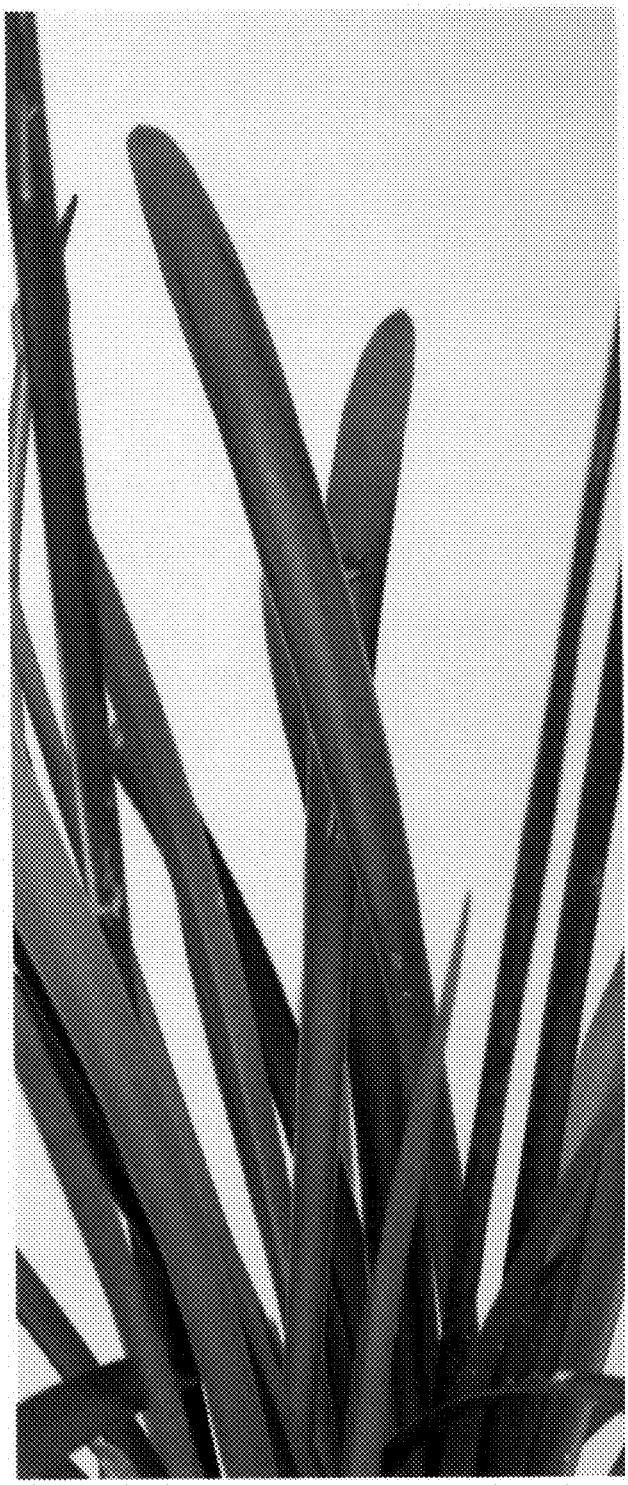

The photograph in FIG. 3 provides a close-up view of the foliage of 'Su Casa'.

The colors in the photographs are as close as possible with the photographic and printing technology utilized and color values cited in the detailed botanical description accurately describe the colors of the new *Agapanthus*.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the effective filing date. Disclosures include website listings by Agapanthuskwekerij, Bowdens Nursery, van Vliet New Plants, Plantariumgroendirekt, R.H.S., Gootjes-Allplant B.V., and Vertigrow.

DETAILED BOTANICAL DESCRIPTION

The following is a detailed description of 19-month-old plants of 'Su Casa' as grown in an unheated poly-covered tunnel in 19-cm containers in Aalter, Belgium. The phenotype of the new cultivar may vary with variations in environmental, climatic, and cultural conditions, as it has not been tested under all possible environmental conditions. The color determinations are in accordance with The 2015 (2019 reprint) Colour Chart of The Royal Horticultural Society, London, England, except where general color terms of ordinary dictionary significance are used.

General description:

*Blooming period*.—End of May to November in Belgium.

*Plant type*.—Semi-deciduous (climate dependent) herbaceous perennial.

*Plant habit*.—Basal rosettes with inflorescences emerging from the rosette center.

*Height and spread*.—Average of 80 cm in height and 50 cm in spread as grown in the landscape.

*Hardiness*.—At least in U.S.D.A. Zones 8 to 12.

*Diseases and pests*.—No susceptibility or resistance to diseases or pests has been observed.

*Root description*.—Thick and fleshy.

*Propagation*.—Division and Tissue culture.

Foliage description:

*Leaf shape*.—Ligulate.

*Leaf division*.—Simple.

*Leaf base*.—Decurrent, cuneate to broadly cuneate.

*Leaf apex*.—Acute.

*Leaf aspect*.—Moderately carinate, slightly to moderately curved.

*Leaf venation*.—Parallel, upper surface; none visible, lower surface; 144A.

*Leaf margins*.—Entire.

*Leaf size*.—Up to 24.1 cm in length and up to 1.3 cm in width.

*Leaf surface*.—Both surfaces non-rugose, upper surface slightly glossy, lower surface very slightly glossy.

*Leaf number*.—Average of 7 leaves per rosette.

*Foliage density*.—Medium.

*Leaf color*.—Young leaves upper surface; 144A, young leaves lower surface; 144A, mature leaves upper surface; a blend of 144A and 146A, mature lower surface; 146B.

*Leaf attachment*.—Sessile to base.

Flower description:

*Inflorescence type*.—Umbel, hemispherical.

*Flower fragrance*.—None.

*Flower type*.—Rotate, campanulate, base of tepals fused.

*Flower number*.—An average of 15 flowers per umbel, 120 buds and flowers per plant.

*Inflorescence size*.—Average of 9.2 cm in height, 19.7 cm in diameter.

*Flower size*.—An average of 3.1 cm in depth, 4.5 cm in diameter, throat 4 mm in diameter, tube length 1.2 cm, tube diameter 5.5 mm.

*Lastingness of inflorescence*.—10 days, self-cleaning.

*Flower aspect*.—Primarily upright.

*Peduncle*.—1 per rosette, very sturdy, oval in shape, held primarily at an angle 70° (0°=soil level), surface is glabrous, slightly glaucous and moderately glossy, an average of 55.8 cm in length and 5 mm in diameter, color; 143A, thin waxy glaucous layer 193D.

*Pedicels*.—Oval in shape, held in multiple angles, surface is glabrous, glossy, average of 5.3 cm in length and 3 mm in diameter, color; upper surface 147A, lower surface 144A.

*Flower buds*.—Oblanceolate in shape, matte surface, slightly velvety, average of 2.1 cm in length and 7 mm in width, color; 94C, axially striped 93A, lower half 92D.

*Tepals* (*perianth*).—6, 2 whorls, rotate, oblanceolate in shape, fused base, entire margins, apex; lower acute, upper bluntly acute, glabrous, slightly velvety, non-rugose, thick substance, 3.8 cm in length, lower tepal 7.5 mm, upper tepal 9 mm, color; when opening upper surface; N155A, base 92D, apex and margins N92A, main vein 93A, area around main vein 93C, when opening lower surface; 94C, darker longitudinal central stripe N92B, apex of outer tepals tinged N92B, fully open upper surface; 91A and 92A, base 92D, around main vein 92A, margins 92A, veins N89B, fully open lower surface; 92A, around main vein 93C, apex of outer tepals 93C, veins N89A.

*Bracts*.—Immature inflorescence bract; 1, dropped when individual flowers develop to open, linear in shape, 2.9 cm in length, 8 mm in width, color; upper surface 163D, base 157A, apex 159D, lower surface 163C, base a blend of 149D and 150C, apex 155D, veins on both surfaces 164B, pedicel bract; 1, filiform in shape, 1.4 cm in length, 0.5 mm in width, color; 187A, apex N187A, base 163C.

Reproductive organs:

*Gynoecium*.—Pistil; 1, average of 1.8 cm in length, stigma; club-shaped, 92B in color, style; 1.7 cm in length, color 92B and 92C and fading towards the base NN155D, ovary; oblong in shape, 1 cm in length, 4 mm in width and 150B in color, pistillodes not present.

*Androecium*.—Stamens; 6, anthers; basifixed, oblong in shape, 2 mm in length, 1 mm in width, N186A in color, filament; 2.2 cm in length, color 94C and fading towards the base 92D, pollen; moderate in quantity and N144C in color, staminodes not present.

*Fruit/seed*.—None observed to date.

It is claimed:

1. A new and distinct cultivar of *Agapanthus* plant named 'Su Casa' as herein illustrated and described.

* * * * *